(12) United States Patent
Halpert

(10) Patent No.: US 6,742,928 B2
(45) Date of Patent: Jun. 1, 2004

(54) DENTAL X-RAY BLOCK

(76) Inventor: Daniel H. Halpert, 10763 Citrus Dr., Moorpark, CA (US) 93021

( * ) Notice: Subject to any disclaimer, the term of this patent is extended or adjusted under 35 U.S.C. 154(b) by 0 days.

(21) Appl. No.: 10/098,944

(22) Filed: Mar. 13, 2002

(65) Prior Publication Data

US 2002/0106057 A1 Aug. 8, 2002

Related U.S. Application Data

(63) Continuation-in-part of application No. 09/422,882, filed on Oct. 21, 1999, now abandoned.

(51) Int. Cl.$^7$ .............................................. G03B 42/02
(52) U.S. Cl. ...................................................... 378/168
(58) Field of Search ................................. 378/168–170

(56) References Cited

U.S. PATENT DOCUMENTS

| | | | |
|---|---|---|---|
| 1,012,561 A | 12/1911 | Ketcham | |
| 1,321,465 A | 11/1919 | MacLagan | |
| 2,010,281 A | 8/1935 | Van Valkenburg | |
| 4,147,662 A | 4/1979 | Schwartz | |
| 4,499,591 A | * 2/1985 | Hartwell | 378/62 |
| 4,852,143 A | 7/1989 | Scheier et al. | |
| 4,922,511 A | * 5/1990 | Gay | 378/169 |
| 4,965,885 A | * 10/1990 | Fuhrmann | 378/168 |
| 5,450,465 A | 9/1995 | Tanaka | |
| 5,466,561 A | 11/1995 | Rantanen | |

OTHER PUBLICATIONS

"Introduction To X–Ray Analysis" Eugene Bertin, Pienum Press, 1978, p 59–60.*

* cited by examiner

*Primary Examiner*—Craig E. Church
(74) *Attorney, Agent, or Firm*—Orrick, Herrington & Sutcliffe LLP

(57) ABSTRACT

A dental x-ray block to eliminate sheets of lead foil from dental x-ray film packets and to inhibit unnecessary x-ray exposure as well as backscattered reflections that can obscure x-ray images and methods of manufacturing and using the same. The dental x-ray block comprises a mouthpiece and a packet holder, which is coupled with the mouthpiece and configured to receive and engage a dental x-ray film packet. Being configured to significantly attenuate and/or absorb x-rays, an attenuation member is coupled with the dental x-ray block and is substantially in axially alignment with the dental x-ray film packet. Therefore, after the dental x-ray film packet has been exposed to a primary x-ray beam, the primary x-ray beam is significantly attenuated by the attenuation member to inhibit unnecessary x-ray exposure and secondary exposures due to backscattered reflections from obscuring x-ray images.

55 Claims, 4 Drawing Sheets

DENTAL X-RAY BLOCK

CROSS-REFERENCE TO RELATED APPLICATIONS

This application is a continuation-in-part of co-pending U.S. patent application Ser. No. 09/422,882, filed on Oct. 21, 1999 ABN. The priority of this prior application is expressly claimed, and its disclosure is hereby incorporated by reference in its entirety.

FIELD OF THE INVENTION

The present invention relates generally to x-ray imaging systems and, more particularly, to a dental x-ray block having a packet support member that is configured to attenuate x-rays.

BACKGROUND OF THE INVENTION

The use of x-rays provides a minimally invasive, yet effective, tool in the diagnosis and treatment of dental conditions. Dental x-rays may be used not only to detect cavities, but also to survey tooth development, to diagnose bone diseases, to evaluate the results of an injury, or to plan orthodontic treatment. These procedures typically are performed by placing a dental x-ray block, including a dental x-ray film packet, into the mouth of a patient and positioning the dental x-ray block adjacent to an area of interest, such as a tooth, within the patient's mouth to be diagnosed and/or treated. An external x-ray source is placed adjacent to and directed toward the area of interest, opposite to the dental x-ray film packet. When activated, the external x-ray source emits a primary x-ray beam, which travels through the area of interest and exposes dental x-ray film within the dental x-ray film packet. After the dental x-ray film has been exposed, the dental x-ray block is removed from the patient's mouth, and the dental x-ray film packet is separated from the dental x-ray block. The dental x-ray film then is extracted from the dental x-ray film packet and developed, producing an x-ray image of the area of interest. Additional x-ray images can be created by repeating the above procedure with other dental x-ray film packets.

The construction of dental x-ray film packets is well-known. A typical dental x-ray film packet includes a single or double sheet of intraoral dental x-ray film as discussed in a book, entitled "Oral Radiology: Principles and Interpretation," by Drs. Goaz and White. With one or both sides coated with emulsion, the dental x-ray film is light-sensitive and is enclosed within an opaque protective wrapper to prevent exposure of the dental x-ray film to light. The protective wrapper, in turn, is placed within a moisture-resistant wrapper with a thin sheet of lead foil that is disposed between the opaque protective wrapper and the moisture-resistant wrapper. When the dental x-ray film packet is positioned adjacent to the area of interest, the sheet of lead foil attenuates the primary x-ray beam that travels beyond the dental x-ray block and toward tissues within the patient's mouth that are immediately adjacent to the area of interest. Thus, the primary x-ray beam, as attenuated, is less likely to unnecessarily expose the adjacent tissues and be reflected by dense structures, such as teeth or bone, within the adjacent tissues, as backscattered reflections that can result in a secondary exposure of the dental x-ray film.

Similarly, dental x-ray blocks for holding x-ray film packets also generally are well-known. For example, U.S. Pat. No. 1,012,561, issued to Ketcham, describes a mouth packet holder to be used for taking x-rays of teeth. A typical dental x-ray block includes a mouthpiece, which is formed from a soft material, and a packet holder. The packet holder is coupled with the mouthpiece and includes a packet retention section and a packet support member, which extends substantially perpendicularly from the mouthpiece. The packet retention section is configured to receive and engage the dental x-ray film packet, which abuts the packet support member when engaged by the packet retention section. Although the dental x-ray film packet is substantially rigid, the packet support member is configured to support the dental x-ray film packet, holding the dental x-ray film packet flat to prevent image distortion. When the packet holder with the dental x-ray film packet is positioned adjacent to an area of interest within the patient's mouth, the mouthpiece is configured to be engaged by the patient's teeth to secure the dental x-ray film packet in place without causing damage to the patient's teeth.

The use of dental x-ray blocks, however, currently suffers from several critical disadvantages. First, although the lead foil within the dental x-ray film packet serves a useful purpose, lead is highly toxic to humans, and children are particularly susceptible to the effects of lead exposure. Even low levels of lead exposure may gravely impact a child's health and intellectual development by impairing his growth, reducing his attention span, and causing learning disabilities. These effects may be long-term and irreversible. Further, lead does not naturally decompose. Once the air, water, or soil in a geographic region has been contaminated, the lead contamination, unless properly removed, can continue indefinitely, poisoning generations of children. Recognizing these risks, some film packet manufacturers have instituted lead-recycling programs, and environmental protection groups have advocated avoiding unnecessary lead usage and removing existing lead contamination.

Second, the sheet of lead foil is not completely opaque to the primary x-ray beam; instead, the typical sheet of lead foil is configured to attenuate the primary x-ray beam only by approximately fifty percent. Therefore, despite the sheet of lead foil, the use of currently-available dental x-ray blocks still permits unnecessarily exposure of the adjacent tissues to a significant portion of the primary x-ray beam, which also can result in the backscattered reflections from the dense structures in the adjacent tissues. Further, upon reaching the dental x-ray block, the backscattered reflections, like the primary x-ray beam, are only partially attenuated by the sheet of lead foil, creating the secondary exposure of the dental x-ray film. Since the backscattered reflections travel at different angles and generally are too weak to produce a second x-ray image, the secondary exposure cause a gray fog to appear on the dental x-ray film, obscuring the x-ray image.

In view of the foregoing, it is believed that a need exists for an improved dental x-ray block that overcomes the aforementioned obstacles and deficiencies of currently-available dental x-ray blocks.

SUMMARY OF THE INVENTION

The present invention is directed to a dental x-ray block having an attenuation member that is configured to attenuate x-rays. A dental x-ray block in accordance with the present invention comprises a mouthpiece and a packet holder. Being manufactured from a material that is substantially transparent to x-rays, the mouthpiece is configured to be received within a patient's mouth and engaged by the patent's teeth. Coupled with the mouthpiece, the packet holder also is manufactured from a material that is substantially transparent to x-rays and is configured to be received within the patient's mouth. The packet holder is configured to receive and engage a dental x-ray film packet and includes an attenuation member. Being substantially axially aligned with the dental x-ray film packet, the attenuation member is configured to significantly attenuate and/or absorb x-rays, preferably having an x-ray attenuation level in excess of approximately fifty percent.

It will be appreciated that a dental x-ray block in accordance with the present invention may serve to alleviate some of the environmental protection and human health concerns regarding lead exposure. As presently used, dental x-ray film packets include dental x-ray film and a sheet of lead foil for preventing unnecessary x-ray exposure and reducing unwanted x-ray reflections. As a result, a sheet of lead foil presently is produced, and must ultimately be disposed of, for each dental x-ray film packet developed. According to the present invention, the attenuation member within the dental x-ray block performs the same functions as the sheet of lead foil and can avoid the lead disposal concerns by facilitating the elimination of the lead foil from the dental x-ray film packets. Thereby, manufacturers of dental x-ray film packets can curtail the amount of lead used, and the contamination of the environment that results from discarded dental x-ray film packets may be reduced. Due to the volume dental x-rays taken annually, the decrease in the aggregate amount of lead released into the environment over time can be substantial.

It also will be appreciated that, through the use of dental x-ray blocks in accordance with the present invention, the manufacturers of dental x-ray film packets may experience reduced production costs. First, the manufacturers can save money by purchasing a smaller amount of lead by eliminating the sheets of lead foil from dental x-ray film packets. Second, by decreasing the amount of lead processed, the consequential costs associated with lead usage, such as the costs for lead handling procedures and lead recycling programs, can also be reduced. These reduced costs may translate into substantial savings in diagnostic and treatment costs that may be passed on to patients required to undergo dental x-ray procedures or to their insurers.

It further will be appreciated that, with the attenuation member having the x-ray attenuation level in excess of approximately fifty percent, the dental x-ray block of the present invention is configured to provide a significantly greater level of x-ray attenuation than the sheet of lead foil within the dental x-ray film packet. Due to the significant level of x-ray attenuation, the dental x-ray block can substantially inhibit unnecessary exposure of tissues within the patient's mouth that are immediately adjacent to an area of interest that is being x-ray imaged. Further, any backscattered reflections of the x-rays from dense structures within the adjacent tissues also pass through the attenuation member of the dental x-ray block to reach the dental x-ray film. Being significantly attenuated by the attenuation member, the backscattered reflections generally are too weak to cause significant secondary exposures of the dental x-ray film. Thus, the x-ray image of the area of interest is not obscured.

Figure 1:
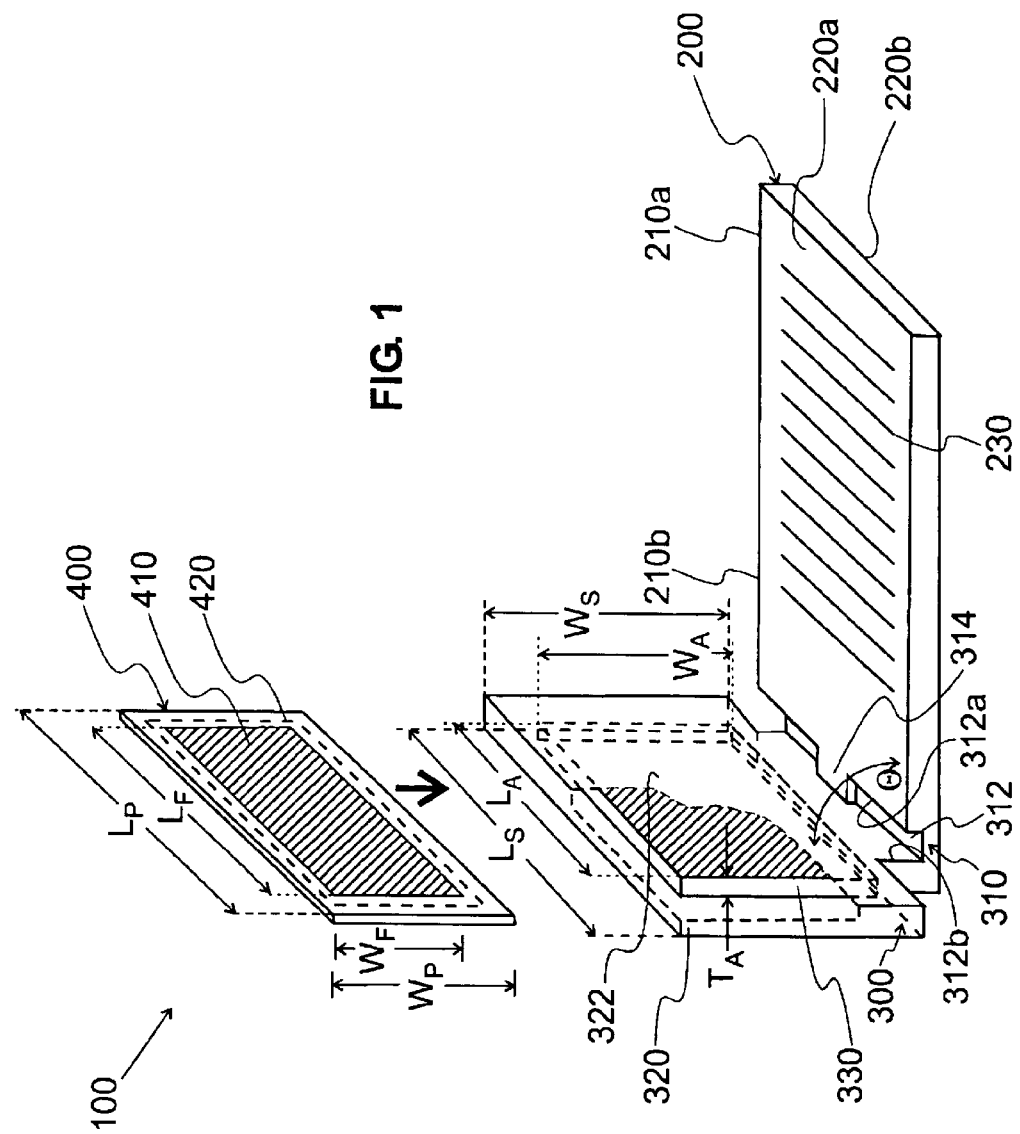
FIG. 1 is an illustration of one preferred embodiment of a dental x-ray block in accordance with the present invention.

It should be noted that the figures are not drawn to scale and that elements of similar structures or functions are represented by like reference numerals throughout the figures. It also should be noted that the figures are only intended to facilitate the description of the preferred embodiments of the present invention. They are not intended as an exhaustive description of the present invention or as a limitation on the scope of the present invention.

DETAILED DESCRIPTION OF THE PREFERRED EMBODIMENTS

Since exposure to lead presents both environmental and health concerns and since currently-available dental x-ray blocks are not sufficient to protect patients from unnecessary x-ray exposure and dental x-ray film from secondary exposure, an inexpensive apparatus to significantly attenuate a primary x-ray beam emitted during x-ray procedures without increasing the lead content of dental x-ray film packets can prove much more desirable and provide a basis for a wide range of dental diagnostic and treatment applications. This result can be achieved, according to one embodiment of the present invention, by employing a dental x-ray block 100 for dental diagnosis and treatment as shown in FIG. 1. The dental x-ray block 100 comprises a mouthpiece 200 and a packet holder 300.

Figure 3:
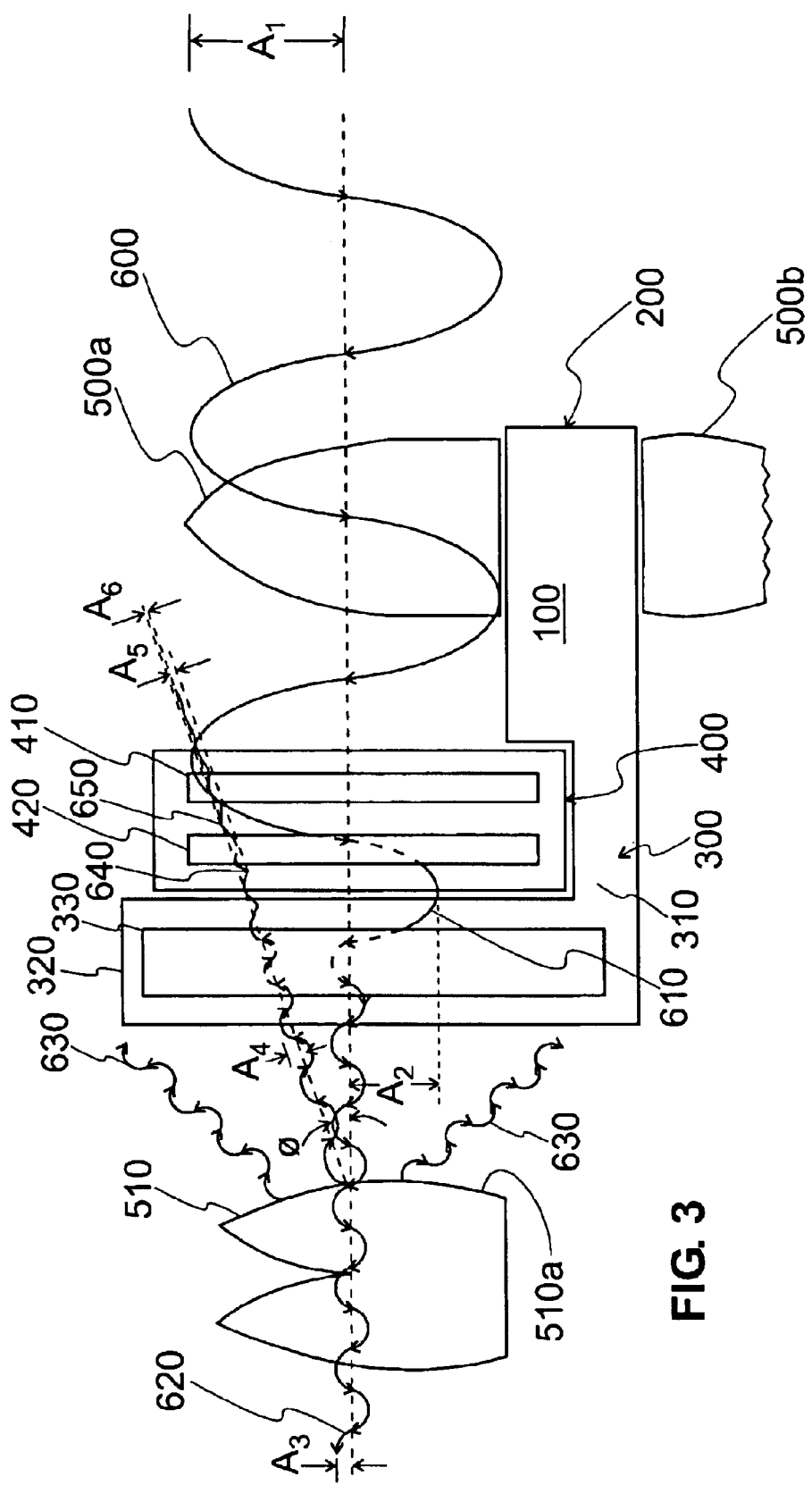
FIG. 3 illustrates the dental x-ray block of FIG. 1 after the dental x-ray block has been positioned onto a patient's mouth.

The mouthpiece 200 is configured to be received, partially or substantially completely, within a patient's mouth (not shown) and engaged by the patent's teeth 500*a–b* (shown in FIG. 3). Although the mouthpiece 200 can be manufactured from any suitable material and in any manner, the material comprising the mouthpiece preferably is substantially transparent to x-rays and relatively soft to prevent damage to the patent's teeth when engaging the mouthpiece 200. For example, the mouthpiece 200 can be formed from and/or coated with a soft material, such as rubber or plastic. Having a proximal end region 210*a* and a distal end region 210*b*, the mouthpiece 200 can be formed with any suitable shape or size, such as the substantially rectangular shape illustrated in FIG. 1, and includes an upper surface 220*a* and a lower surface 220*b*. The upper surface 220*a* and/or the lower surface 220*b* can include a plurality of stabilization members 230, such as substantially parallel bumps or grooves, which are configured to stabilize the dental x-ray block 100 in the patient's mouth.

Also being configured to be received within the patient's mouth, the packet holder 300 is coupled with the distal end region 210*b* of the mouthpiece 200 in any manner, including fixedly, adjustably, and/or removably, and includes a packet retention member 310 and a packet support member 320. Being disposed substantially between the mouthpiece 200 and the packet support member 320, the packet retention member 310 is configured to receive and engage a conventional dental x-ray film packet 400, typically comprising dental x-ray film 410 and a sheet of lead foil 420. Capable of being manufactured from any suitable material and in any manner, the packet retention member 310 preferably is manufactured from a material that is substantially transparent to x-rays and that is sufficiently flexible to facilitate receipt, engagement, and removal of dental x-ray film packets 400 with thicknesses within a preselected range. For example, the packet retention member 310 can be formed on or within the packet holder 300 and can comprise a channel 312, as illustrated in FIG. 1. In other words, the packet retention member 310 and the packet holder 300, along with the mouthpiece 200, can be formed from substantially the same material and/or can comprise a single unit. Being configured to receive the dental x-ray film packet 400, the channel 312 can be formed with any suitable dimension and by any manner known in the art, such as by molding, and is defined by one or more inner surfaces 312a–b. The channel 312 also is configured to engage the dental x-ray film packet 400 in any manner, such as frictionally or adhesively. The channel 312 can be appropriately dimensioned such that one or more of the inner surfaces 312a–b is configured to engage the dental x-ray film packet 400, and/or the channel 312 can include an engaging member 314 as shown in FIG. 1. The engaging member 314 extends into the channel 312 preferably from the inner surface 312a, which is substantially opposite the packet support member 320, and is configured to engage the dental x-ray film packet 400 in any manner, such as by pressing the dental x-ray film packet 400 against the packet support member 320 and/or the inner surface 312b.

Figure 2:
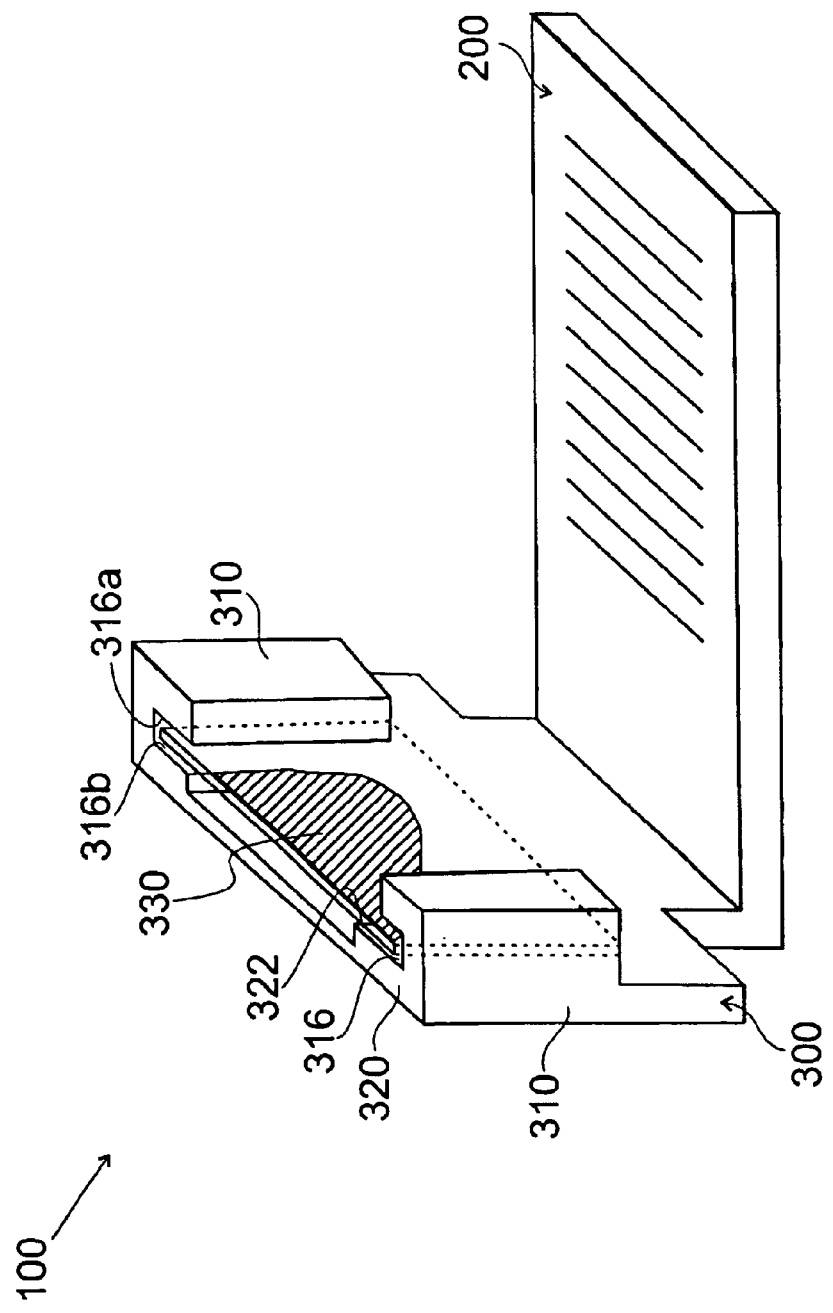
FIG. 2 is an illustration of a second preferred embodiment of a dental x-ray block in accordance with the present invention.

The packet retention member 310 also can be manufactured on the packet support member 320 as shown in FIG. 2. The packet retention member 310 can be coupled with the packet support member 320 in any manner and includes one or more inner surfaces 316a–b that define one or more channels 316. Being formed with any suitable dimension and by any manner known in the art, the channels 316 are configured to receive the dental x-ray film packet 400. Once the dental x-ray film packet 400 has been received, the channel 316 is configured to engage the dental x-ray film packet 400 in any manner, such as frictionally and/or adhesively. For example, the dental x-ray film packet 400 can be disposed between, and frictionally engaged by, the inner surface 316a and the inner surface 316b and/or the packet support member 320, which are substantially opposite the inner surface 316a. If desired, the packet retention member 310 and the packet support member 320 can be formed from substantially the same material and/or can comprise a single unit.

Returning to FIG. 1, the packet support member 320 can be coupled with the packet holder 300 in any manner. The packet support member 320 extends from the packet holder 300, forming a preselected angle θ with the mouthpiece 200, and includes a substantially flat surface 322. Preferably being substantially equal to a right angle, the preselected angle θ can comprise any angle. The substantially flat surface 322 is disposed adjacent to the packet retention member 310 and is configured to support, without bending, the dental x-ray film packet 400. Although the packet support member 320 can be manufactured with any suitable dimensions, the packet support member 320 preferably is of a size and shape that is greater than or substantially equal to a size and shape of the dental x-ray film packet 400. For example, if the packet support member 320 and the dental x-ray film packet 400 each are substantially rectangular as shown in FIG. 1, a length $L_S$ and a width $W_S$ of the packet support member 320 preferably are respectively greater than or substantially equal to a length $L_P$ and a width $W_P$ of the dental x-ray film packet 400. If desired, the packet support member 320 can be removably coupled with the packet holder 300 to facilitate use of a plurality of packet support members 320 with the dental x-ray block 100 of the present invention. Being manufactured with diverse shapes and sizes, the plurality packet support members 320 can be used to adapt the dental x-ray block 100 for use with dental x-ray film packets 400 with various shapes and sizes. The packet support member 320 also can be formed from a material that is substantially pliable such that the packet support member 320 is configured to conform with the various shapes and sizes of the dental x-ray film packets 400.

The packet support member 320 is configured to significantly attenuate and/or absorb x-rays and can be manufactured from any suitable material and in any manner. For example, the packet support member 320 can be manufactured from, or otherwise provided with, an attenuating material, such as a metal or alloy like lead or stainless steel, that can significantly attenuate x-rays. Although the attenuating material can comprise any type of material that can significantly attenuate x-rays, the attenuating material preferably comprises a thermoplastic compound, such as the nontoxic thermoplastic composite material available as part number NJ-96TP/000 from Ecomass Technologies in Austin, Tex. The attenuating material can be disposed within the packet support member 320 and/or on any external surface, such as the substantially flat surface 322, of the packet support member 320 in any manner, such as by molding. Stated somewhat differently, the attenuating material can comprise a coating that can be applied to any external surface of the packet support member 320 and/or an attenuation member 330, which can be disposed substantially completely, as shown in FIG. 1, or partially within the packet support member 320. Preferably, the attenuating material is substantially in axial alignment with the dental x-ray film 410, when the dental x-ray film packet 400 is properly positioned within the dental x-ray block 100.

Although the attenuating material can be manufactured with any suitable dimensions, the attenuating material preferably is of a size and shape that is greater than or substantially equal to a size and shape of the dental x-ray film 410. If the attenuating material and the sheet of dental x-ray film 410 each are substantially rectangular as shown in FIG. 1, for example, a length $L_A$ and a width $W_A$ of the attenuating material can be respectively greater than or substantially equal to a length $L_F$ and a width $W_F$ of the dental x-ray film 410. Further, the size and shape of the attenuating material preferably is greater than or substantially equal to the size and shape of the packet support member 320 to optimize the x-ray attenuation of the packet support member 320. The attenuating material can be removably disposed on or within the packet support member 320 such that a plurality of attenuating materials with differing sizes, shapes, and/or compositions can be disposed on or within the packet support member 320.

Further, to achieve a preselected level of x-ray attenuation, a thickness $T_A$ of the attenuating material can have any suitable dimension and preferably is substantially uniform. The thickness $T_A$ of the attenuating material is sufficient to achieve x-ray attenuation levels in excess of approximately fifty percent and preferably over about ninety percent. If the attenuating material comprises stainless steel, for example, the attenuation member 330 can have the thickness $T_A$ of substantially 0.5 mm. Being disposed on or within the packet support member 320, the attenuating material can have the thickness $T_A$ that is much greater than a thickness of the sheet of lead foil 420, which is limited by the dental x-ray film packet 400. The x-ray attenuation levels of the packet support member 320 therefore can be substantially greater than an x-ray attenuation level of the sheet of lead foil 420, which typically is approximately equal to fifty percent. Since the x-ray attenuation levels of the packet support member 320 can exceed the x-ray attenuation level of the sheet of lead foil 420, the dental x-ray block 100 of the present invention is compatible for use with dental x-ray film packets 400 that do not include the sheet of lead foil 420. By eliminating the sheet of lead foil 420 from the dental x-ray film packets 400, fewer sheets of lead foil 420 will need to be manufactured, handled, and disposed of, thereby reducing the risk of lead exposure and environmental contamination.

Turning to FIG. 3, to create an x-ray image (not shown) of an area of interest, such as the tooth 500a, the dental x-ray film packet 400 is received and engaged by the packet retention member 310 and is supported by the packet support member 320 in the manner that was described in more detail above. The sheet of lead foil 420 within the dental x-ray film packet 400, if present, preferably is disposed substantially between the dental x-ray film 410 of the dental x-ray film packet 400 and the packet support member 320. The packet holder 300 then is received within the patient's mouth, and the dental x-ray film packet 400 is positioned adjacent to the tooth 500a. When the dental x-ray film packet 400 has been properly positioned, the mouthpiece 200 extends between, and is engaged by, the patent's teeth 500a–b to maintain the position of the dental x-ray film packet 400. An external x-ray source (not shown) is positioned outside the patient's mouth and adjacent to the tooth 500a such that the tooth 500a is disposed substantially between the external x-ray source and the dental x-ray film packet 400. Being directed substantially toward the tooth 500a, the external x-ray source is configured to generate a primary x-ray beam 600 when activated. The primary x-ray beam 600 comprises a plurality of x-ray beams that are substantially parallel and that have a preselected amplitude $A_1$.

When the external x-ray source is momentarily activated, the external x-ray source emits the primary x-ray beam 600, which propagates toward the tooth 500a. The primary x-ray beam 600 passes through the tooth 500a and exposes the dental x-ray film 410, striking the dental x-ray film 410 with substantially uniform direction and geometry to impart the x-ray image of the tooth 500a. Upon passing through the dental x-ray film 410, the primary x-ray beam 600 reaches the sheet of lead foil 420, which attenuates the primary x-ray beam 600 to produce an attenuated x-ray beam 610, which, like the primary x-ray beam 600, comprises a plurality of x-ray beams that are substantially parallel. The attenuated x-ray beam 610 has an amplitude $A_2$ that is approximately equal to a product of the preselected amplitude $A_1$ of the primary x-ray beam 600 and the x-ray attenuation level of the sheet of lead foil 420. Since the typical sheet of lead foil 420 has the x-ray attenuation level of about fifty percent, the amplitude $A_2$ of the attenuated x-ray beam 610 is about one-half of the preselected amplitude $A_1$.

The attenuated x-ray beam 610 travels from the sheet of lead foil 420 and traverses the packet support member 320. Encountering the attenuating material of the packet support member 320, the attenuated x-ray beam 610 is further-attenuated, resulting in a further-attenuated x-ray beam 620 of substantially parallel x-ray beams and with an amplitude $A_3$. For example, if the attenuating material has an x-ray attenuation level of approximately ninety percent, the amplitude $A_3$ of the attenuated x-ray beam 610 is approximately one-tenth of the amplitude $A_2$ of the attenuated x-ray beam 610 or one-twentieth of the preselected amplitude $A_1$ of the primary x-ray beam 610. The further-attenuated x-ray beam 620 propagates from the packet support member 320 and exposes adjacent tissues (not shown) in the patient's mouth. In contrast to conventional x-ray techniques, which permit exposure to one-half of the primary x-ray beam 600, the attenuating material of the dental x-ray block 100 of the present invention inhibits the adjacent tissues from being exposed to a significant portion of the primary x-ray beam 600.

Further, the dental x-ray block 100 of the present invention permits a less significant portion of the primary x-ray beam to be reflected from dense structures, such as teeth 510 or bone, within the adjacent tissues than conventional dental x-ray techniques. Upon reaching the teeth 510, the further-attenuated x-ray beam 620 reflects from one or more external surfaces 510a of the teeth 510 as backscattered reflections 630. The backscattered reflections 630 have an amplitude $A_4$ that is substantially equal to the amplitude $A_3$ of the further-attenuated x-ray beam 620 but comprises divergent x-ray beams, propagating at differing angles $\phi$, because the external surfaces 510a generally are not flat. Diverging from the external surfaces 510a, only a portion of the backscattered reflections 630 are directed back toward the dental x-ray film packet 400 and, upon reaching the dental x-ray block 100, traverse the packet support member 320. The attenuating material of the packet support member 320 attenuates the relevant backscattered reflections 630, producing attenuated backscattered reflections 640 with an amplitude $A_5$ that is approximately one-tenth of the amplitude $A_4$ of the backscattered reflections 630 or one-two-hundredth of the preselected amplitude $A_1$ of the primary x-ray beam 610. When the attenuated backscattered reflections 640 reach the dental x-ray film packet 400, the sheet of lead foil 420 further attenuates the attenuated backscattered reflections 640 resulting in further-attenuated backscattered reflections 650. The further-attenuated backscattered reflections 650 have an amplitude $A_6$ that is approximately one-half of the amplitude $A_5$ of the attenuated backscattered reflections 640, or one-four-hundredth of the preselected amplitude $A_1$ of the primary x-ray beam 610, because the typical sheet of lead foil 420 has the x-ray attenuation level of about fifty percent.

Upon traversing the sheet of lead foil 420, the further-attenuated backscattered reflections 650 pass through the dental x-ray film 410, potentially resulting in secondary exposures. Striking the dental x-ray film 410 at the differing angles $\phi$ and with different geometries, the further-attenuated backscattered reflections 650, with the amplitude $A_6$ that is less than one percent the preselected amplitude $A_1$ of the primary x-ray beam 610, generally are too weak to cause significant secondary exposures. In contrast to conventional dental x-ray techniques with backscattered reflections that retain about twenty-five percent of the preselected amplitude $A_1$ of the primary x-ray beam 610, the secondary exposures from the further-attenuated backscattered reflections 650 do not cause a gray fog to appear on the dental x-ray film 410. Accordingly, the x-ray image is not obscured. After the x-ray procedure is completed, the dental x-ray film packet 400 can be disassembled, and the dental x-ray film 410 can be removed and developed to produce a visible x-ray image of the area of the tooth 500a.

Figure 4:
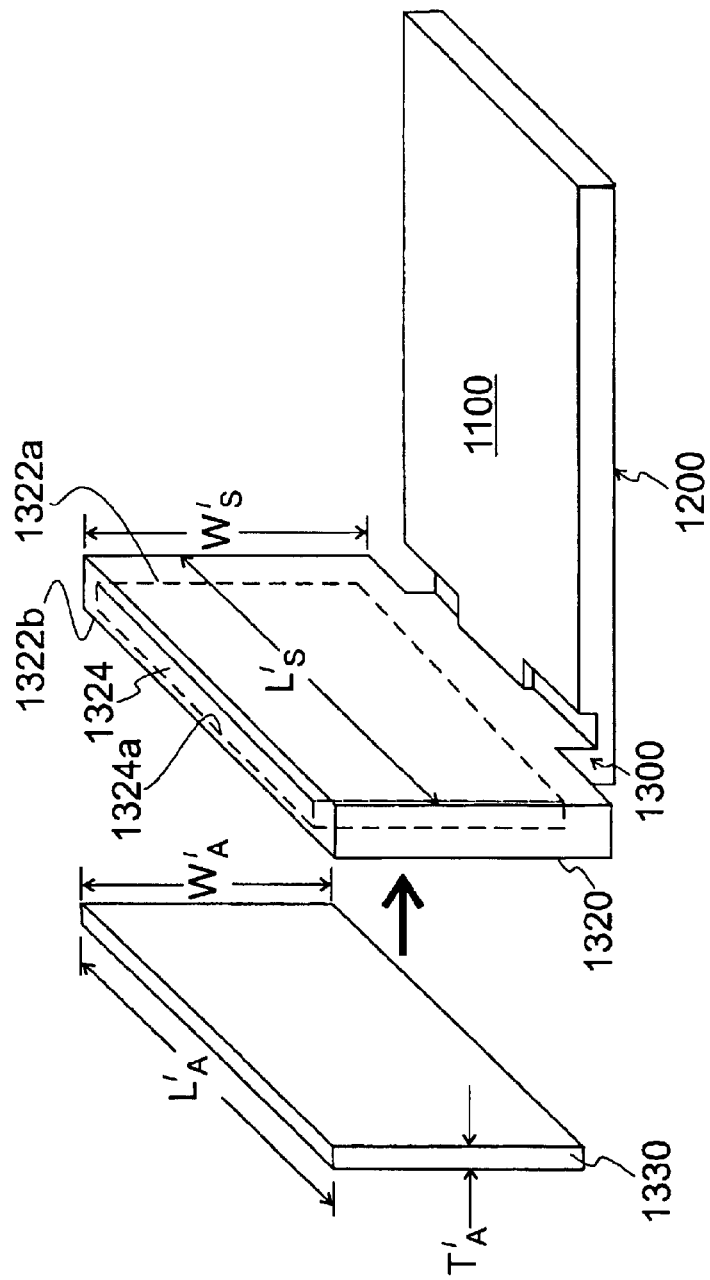
FIG. 4 is an illustration of one preferred embodiment of an attenuation member for a commercially-available dental x-ray block in accordance with the present invention.

It will be appreciated that a commercially-available dental x-ray block 1100 can be adapted to incorporate the concepts of the present invention as illustrated in FIG. 4. For example, an attenuation member 1330 can be coupled with the dental x-ray block 1100, which comprises a mouthpiece 1200 and a packet holder 1300. Being produced in the manner described above with respect to the mouthpiece 200, the mouthpiece 1200 is configured to be received within a patient's mouth (not shown) and engaged by the patent's teeth 500a–b (shown in FIG. 3). Similarly, the packet holder 1300 is configured to be received within the patient's mouth and is produced in the manner described above with respect to the packet holder 300, being coupled with the mouthpiece 1200 and being configured to receive and engage a dental x-ray film packet 400 (shown in FIG. 1). The packet holder 1300 can engage the dental x-ray film packet 400 in any manner and may include a packet support member 1320. If present, the packet support member 1320 is configured to support, without bending, the dental x-ray film packet 400 and is produced in the manner described above with respect to the packet support member 320.

Being configured to significantly attenuate and/or absorb x-rays, the attenuation member 1330 can be manufactured in any manner and from any suitable material, including the attenuating material described above with respect to the packet support member 320. The attenuation member 1330 can be coupled with the dental x-ray block 1100 in any manner and, when the dental x-ray film packet 400 is properly positioned within the dental x-ray block 1100, preferably is substantially in axial alignment with dental x-ray film 410 (shown in FIG. 1) within the dental x-ray film packet 400. Although the attenuation member 1330 can be manufactured with any suitable dimensions, the attenuation member 1330 preferably is of a size and shape that is greater than or substantially equal to a size and shape of the dental x-ray film 410. If the attenuation member 1330 and the sheet of dental x-ray film 410 each are substantially rectangular as shown in FIG. 4, for example, a length $L_A'$ and a width $W_A'$ of the attenuation member 1330 can be respectively greater than or substantially equal to a length $L_F$ (shown in FIG. 1) and a width $W_F$ (shown in FIG. 1) of the dental x-ray film 410. Further, the size and shape of the attenuation member 1330 preferably is greater than or substantially equal to a size and shape of the packet support member 1320, if any, to optimize x-ray attenuation. Continuing with the above example, the length $L_A'$ and the width $W_A'$ of the attenuation member 1330 can be respectively greater than or substantially equal to a length $L_S'$ and a width $W_S'$ of the packet support member 1320.

As was discussed in more detail above with respect to the packet support member 320, the attenuation member 1330 can be disposed within the packet support member 1320 in any manner. For example, an opening 1324 can be formed in the packet support member 1320 and defined by one or more inner surfaces 1324a. Being configured to receive the attenuation member 1330, the opening 1324 can be formed in any manner and with any suitable shape and size, such that the attenuation member 1330 is partially or substantially completely disposed within the opening 1324. The attenuation member 1330 can be fixedly or removably retained within the opening 1324 by engaging the inner surfaces 1324a in any manner, such as frictionally and/or adhesively. Preferably being disposed on an external surface 1322b that is substantially opposite the dental x-ray film packet 400, the attenuation member 1330 also can be disposed on one or more external surface 1322a–b of the packet support member 1320 in any manner, such as a coating. If formed substantially as a plate as illustrated in FIG. 4, for example, the attenuation member 1330 can be coupled with at least one of the external surfaces 1322a–b in any manner, including frictionally and/or adhesively. Although the attenuation member 1330 preferably is disposed on or within the packet support member 1320, the attenuation member 1330 can be coupled with the mouthpiece 1200 and/or the packet holder 1300 in any manner. For example, the attenuation member 1330 can be coupled with the mouthpiece 1200 via a fastener (not shown) that is formed from a material that preferably is substantially transparent to x-rays.

Further, to achieve a preselected level of x-ray attenuation, a thickness $T_A'$ of the attenuation member 1330 can have any suitable dimension and preferably is substantially uniform. The thickness $T_A'$ of the attenuation member 1330 preferably is sufficient to achieve x-ray attenuation levels of at least approximately fifty percent or, more preferably, ninety percent. Being disposed on or within the dental x-ray block 1100, the attenuation member 1330 can have the thickness $T_A'$ that is much greater than a thickness of the sheet of lead foil 420, which is limited by the dental x-ray film packet 400. The x-ray attenuation levels of the packet support member 320 therefore can be substantially greater than an x-ray attenuation level of the sheet of lead foil 420, which typically is approximately equal to fifty percent. Since the x-ray attenuation levels of the packet support member 320 can exceed the x-ray attenuation level of the sheet of lead foil 420, the dental x-ray block 100 of the present invention is compatible for use with dental x-ray film packets 400 that do not include the sheet of lead foil 420. By eliminating the sheet of lead foil 420 from the dental x-ray film packets 400, fewer sheets of lead foil 420 will need to be manufactured, handled, and disposed of, thereby reducing the risk of lead exposure and environmental contamination.

It also will be appreciated that the concepts of the present invention are compatible with any type of x-ray imaging system, including digital x-ray imaging systems. In contrast to conventional x-ray imaging systems, a typical digital x-ray imaging system employs a sensor assembly (not shown) that is disposed within a moisture-resistant package and includes a plurality of image sensors, rather than dental x-ray film 410 (shown in FIG. 1). Being arranged on the sensor assembly in any manner, such as any one-dimensional or two-dimensional array, the plurality of image sensors can comprise any type of image sensors, preferably being solid-state electronic devices such as charge-coupled devices (CCDs) and/or photostimuable phosphors (PSPs). In response to being exposed to x-rays, the plurality of image sensors each is configured to generate a signal (not shown) that is substantially proportional to the x-ray exposure level. The signals can comprise any type of signals, including analog signals, and are communicated to an image processing system (not shown), which is configured to assemble and convert the signals into an x-ray image. The x-ray image, in turn, can be visually present in any manner; for example, the signals can be converted into a standard video format such that the x-ray image can be presented on any standard video system.

To create an x-ray image of an area of interest in a patient's mouth, the digital x-ray imaging system can be provided with a dental x-ray block (not shown) having an attenuation member (not shown) that is configured to significantly attenuate and/or absorb x-rays in the manner described above with respect to the attenuating material of the packet support member 320 (shown in FIG. 1). The dental x-ray block is produced in the manner described above with respect to the dental x-ray block 100 (shown in FIG. 1) and/or the dental x-ray block 1100 (shown in FIG. 4), having a mouthpiece that is coupled with a packet holder. The package enclosing the sensor assembly is received and engaged by the packet holder in the manner described above with respect to the dental x-ray film packet 400 (shown in FIG. 1). The packet holder then is received within the patient's mouth, and, when the package enclosing the sensor assembly is positioned substantially adjacent to the area of interest, the mouthpiece extends between, and is engaged by, the patent's teeth. An external x-ray source (not shown) is positioned outside the patient's mouth and adjacent to the area of interest such that the area of interest is disposed substantially between the external x-ray source and the package enclosing the sensor assembly. Being directed substantially toward the area of interest, the external x-ray source is configured to generate a primary x-ray beam (not shown) when activated.

When the external x-ray source is momentarily activated, the primary x-ray beam passes through the area of interest and exposes the sensor assembly, generating the plurality of signals that can be assembled and converted into the x-ray image. Since the typical package enclosing the sensor assembly does not include a sheet of lead foil, the primary x-ray beam, upon traversing the sensor assembly, encounters the attenuation member. Being significantly attenuated by the attenuation member in the manner described in more detail above, the primary x-ray beam, as attenuated, travels from the attenuation member and exposes adjacent tissues (not shown) in the patient's mouth. In contrast to current digital x-ray imaging techniques, which permit exposure to the unattenuated primary x-ray beam, the attenuation member inhibits the adjacent tissues from being exposed to a significant portion of the primary x-ray beam. Further, the attenuation member of the dental x-ray block prevents a significant portion of the primary x-ray beam from being reflected as backscattered reflections from dense structures within the adjacent tissues than present digital x-ray imaging techniques. Upon reaching the dental x-ray block, the relevant backscattered reflections are attenuated by the attenuation member. When the attenuated backscattered reflections reach the package enclosing the sensor assembly, the attenuated backscattered reflections pass through the sensor assembly, potentially resulting in secondary exposures. Due to the significant attenuation of the attenuation member, however, the attenuated backscattered reflections generally are too weak to cause significant secondary exposures such that the x-ray image is not obscured.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

What is claimed is:

1. A dental x-ray block, comprising:
   a mouthpiece;
   a packet holder, said packet holder being coupled with said mouthpiece and being configured to receive and engage a dental x-ray film packet; and
   an attenuation member, said attenuation member being removably coupled with said packet holder and being configured to be substantially in axial alignment with the dental x-ray film packet when the dental x-ray packet is received by said packet holder,
   wherein said attenuation member is configured to attenuate at least substantially fifty percent of the enemy of an incident x-ray beam.

2. The dental x-ray block of claim 1, wherein said attenuation member is configured to attenuate at least substantially ninety percent of the energy of the incident x-ray beam.

3. The dental x-ray block of claim 1, wherein said attenuation member is configured to attenuate less than substantially ninety-nine percent of the energy of the incident x-ray beam.

4. The dental x-ray block of claim 1, wherein said attenuation member is configured to attenuate at least substantially seventy percent of the energy of the incident x-ray beam.

5. The dental x-ray block of claim 1, wherein said attenuation member is configured to attenuate less than substantially seventy percent of the energy of the incident x-ray beam.

6. The dental x-ray block of claim 1, wherein said packet holder is configured to receive and engage a dental x-ray film packet that excludes a sheet of lead foil.

7. A dental x-ray block, comprising:
   a mouthpiece;
   a packet holder, said packet holder being coupled with said mouthpiece and being configured to receive a dental x-ray packet; and
   attenuating material, said attenuating material being removably coupled with said packet holder, being configured to attenuate substantially between fifty percent and ninety percent of the energy of an incident x-ray beam, and being configured to be substantially in axial alignment with the dental x-ray packet when the dental x-ray packet is received by said packet holder.

8. The dental x-ray block of claim 7, wherein said attenuating material is configured to substantially inhibit unnecessary x-ray exposure.

9. The dental x-ray block of claim 7, wherein said attenuating material is formed on said packet holder.

10. The dental x-ray block of claim 7, wherein said attenuating material extends from said packet holder.

11. The dental x-ray block of claim 7, wherein said packet holder includes a packet retention member and a packet support member, said packet retention member being disposed substantially between said mouthpiece and said packet support member.

12. The dental x-ray block of claim 11, wherein said attenuating material is disposed on said packet support member.

13. The dental x-ray block of claim 11, wherein said attenuating material is disposed within said packet support member.

14. The dental x-ray block of claim 11, wherein said attenuating material comprises said packet support member.

15. The dental x-ray block of claim 7, wherein said attenuating material has a thickness that is greater than or equal to approximately 0.5 mm.

16. The dental x-ray block of claim 7, wherein said attenuating material has a thickness that is substantially uniform.

17. The dental x-ray block of claim 7, wherein said attenuating material comprises a metal.

18. The dental x-ray block of claim 17, wherein said attenuating material comprises lead.

19. The dental x-ray block of claim 17, wherein said attenuating material comprises steel.

20. The dental x-ray block of claim 7, wherein said attenuating material comprises a thermoplastic compound.

21. The dental x-ray block of claim 7, wherein said attenuating material comprises a coating.

22. The dental x-ray block of claim 7, wherein said attenuating material and said packet holder are coupled via an adhesive.

23. The dental x-ray block of claim 7, wherein said attenuating material and said packet holder are frictionally coupled.

24. A system for producing x-ray images, comprising:
    a dental x-ray packet;

a dental x-ray block, said dental x-ray block being configured to receive said dental x-ray packet;

an x-ray source, said x-ray source being directed substantially toward said dental x-ray packet and being configured to generate a primary x-ray beam; and attenuating material, said attenuating material being removably coupled with said dental x-ray block and being configured to attenuate the energy of said primary x-ray beam by at least substantially fifty percent, said dental x-ray packet being disposed substantially between said attenuating material and said x-ray source.

25. The system of claim 24, wherein said dental x-ray packet includes a sensor assembly.

26. The dental x-ray block of claim 25, wherein the sensor assembly comprises at least one charge-coupled device.

27. The dental x-ray block of claim 25, wherein the sensor assembly comprises at least one photostimuable phosphor.

28. The dental x-ray block of claim 25, wherein the dental x-ray packet excludes a sheet of lead foil.

29. The dental x-ray block of claim 25, wherein said attenuating material has a preselected size, said preselected size being greater than or substantially equal to a predetermined size of the sensor assembly.

30. The dental x-ray block of claim 24, wherein said attenuating material is configured to eliminate a need for a sheet of lead foil from the dental x-ray packet.

31. The dental x-ray block of claim 7, wherein said attenuating material is configured to substantially inhibit backscattered reflections from creating secondary exposures of the dental x-ray packet.

32. The system of claim 24, wherein said dental x-ray packet excludes a sheet of lead foil.

33. The system of claim 24, wherein said attenuating material is disposed on said dental x-ray block.

34. The system of claim 24, wherein said attenuating material is disposed within said dental x-ray block.

35. The system of claim 24, wherein said attenuating material is configured to attenuate the energy of said primary x-ray beam by at least substantially ninety percent.

36. The system of claim 24, wherein said attenuating material is configured to attenuate the energy of said primary x-ray beam by less than substantially ninety-nine percent.

37. The system of claim 24, wherein said dental x-ray packet includes dental x-ray film.

38. The system of claim 24, wherein said attenuating material has a preselected size, said preselected size being greater than or substantially equal to a predetermined size of said dental x-ray packet.

39. A method for producing x-ray images, comprising:
providing a dental x-ray packet;
disposing said dental x-ray packet in a dental x-ray block;
positioning said dental x-ray packet substantially adjacent to an area of interest in a patent's mouth;
exposing dental x-ray film within said dental x-ray packet to a primary x-ray beam;
attenuating the energy of said primary x-ray beam via a sheet of lead foil within said dental x-ray packet to form an attenuated primary x-ray beam;
further attenuating the energy of said attenuated primary x-ray beam by substantially between ninety percent and ninety-nine percent via an attenuation member, being removably coupled with said dental x-ray block, to form a further-attenuated primary x-ray beam such that said further-attenuated primary x-ray beam is inhibited from exposing tissues within the patient's mouth and adjacent to the area of interest, said attenuation member being coupled with said dental x-ray block and being substantially in axial alignment with said dental x-ray film;
attenuating the energy of backscatter reflections of said further-attenuated primary x-ray beam by substantially between ninety percent and ninety-nine percent via said attenuation member to form attenuated backscatter reflections, said backscatter reflections being formed when said further-attenuated primary x-ray beam reflects from a dense structure in the tissues within the patient's mouth; and
attenuating the energy of said attenuated backscatter reflections via said sheet of lead foil to form further-attenuated backscatter reflections such that said further-attenuated backscatter reflections are inhibited from creating a secondary exposure on said dental x-ray film.

40. A dental x-ray block, comprising:
a mouthpiece;
a packet holder, said packet holder being coupled with said mouthpiece and including a packet retention member and a packet support member, said packet retention member being configured to receive a dental x-ray film packet and being disposed substantially between said mouthpiece and said packet support member; and
an attenuation member, said attenuation member being removably coupled with said packet support member, being configured to attenuate substantially between ninety percent and ninety-nine percent of the energy of an incident x-ray beam, and having a preselected size that is greater than or substantially equal to a size of dental x-ray film within the dental x-ray film packet,
wherein said attenuation member is configured to eliminate a sheet of lead foil from the dental x-ray film packet and to substantially inhibit unnecessary x-ray exposure and backscattered reflections from creating secondary exposures of the dental x-ray film.

41. A method for producing x-ray images, comprising:
disposing a dental x-ray packet in a dental x-ray block;
positioning said dental x-ray packet substantially adjacent to an area of interest in a patent's mouth;
exposing said dental x-ray packet to a primary x-ray beam; and
attenuating the energy of said primary x-ray beam by at least substantially fifty percent via attenuation means being removably coupled with said dental x-ray block.

42. The method of claim 41, wherein exposing a dental x-ray packet comprises exposing dental x-ray film within said dental x-ray packet to said primary x-ray beam.

43. The method of claim 41, wherein exposing a dental x-ray packet comprises exposing a sensor assembly within said dental x-ray packet to said primary x-ray beam.

44. The method of claim 41, wherein attenuating the energy of said primary x-ray beam comprises attenuating the energy of said primary x-ray beam by at least substantially ninety percent.

45. The method of claim 41, wherein attenuating the energy of said primary x-ray beam comprises attenuating the energy of said primary x-ray beam by less than substantially ninety-nine percent.

46. The method of claim 41, wherein attenuating the energy of said primary x-ray beam includes attenuating the energy of said primary x-ray beam via a sheet of lead foil within said dental x-ray packet.

47. The method of claim 41, wherein attenuating the energy of said primary x-ray beam includes attenuating the energy of said primary x-ray beam via attenuating material, said attenuating material being coupled with said dental x-ray block and being substantially in axial alignment with said dental x-ray packet.

48. The method of claim 41, wherein attenuating the energy of said primary x-ray beam includes inhibiting said primary x-ray beam from exposing tissues within the patient's mouth and adjacent to the area of interest.

49. The method of claim 48, includes inhibiting said primary x-ray beam from reflecting from a dense structure in the tissues as backscattered reflections.

50. The method of claim 49, further comprising attenuating the energy of said backscattered reflections by at least substantially fifty percent.

51. The method of claim 50, wherein attenuating the energy of said backscattered reflections comprises attenuating the energy of said backscattered reflections by at least substantially ninety percent.

52. The method of claim 50, wherein attenuating the energy of said backscattered reflections comprises attenuating the energy of said backscattered reflections by less than substantially ninety-nine percent.

53. The method of claim 50, wherein attenuating the energy of said backscattered reflections includes attenuating the energy of said backscattered reflections via a sheet of lead foil within said dental x-ray packet.

54. The method of claim 50, wherein attenuating the energy of said backscattered reflections includes attenuating the energy of said backscattered reflections via said attenuating material, said attenuating material being coupled with said dental x-ray block and being substantially in axial alignment with said dental x-ray packet.

55. The method of claim 50, wherein attenuating the energy of said backscattered reflections includes inhibiting said backscattered reflections from creating a secondary exposure of said dental x-ray packet.

* * * * *